United States Patent
Khosrowshahi et al.

(10) Patent No.: US 9,895,102 B2
(45) Date of Patent: Feb. 20, 2018

(54) NON-INVASIVE METHOD OF DIAGNOSING DYSPHAGIA IN PATIENTS HAVING A TRACHEOSTOMY

(71) Applicants: Hamid Khosrowshahi, Tarrytown, NY (US); Gerald W. Gentile, Yonkers, NY (US)

(72) Inventors: Hamid Khosrowshahi, Tarrytown, NY (US); Gerald W. Gentile, Yonkers, NY (US)

(73) Assignee: Flosure Technologies LLC, Tarrytown, NY (US)

( * ) Notice: Subject to any disclaimer, the term of this patent is extended or adjusted under 35 U.S.C. 154(b) by 0 days.

(21) Appl. No.: 15/368,561

(22) Filed: Dec. 2, 2016

(65) Prior Publication Data
US 2017/0188935 A1    Jul. 6, 2017

Related U.S. Application Data

(60) Provisional application No. 62/262,150, filed on Dec. 2, 2015, provisional application No. 62/273,153, filed on Dec. 30, 2015.

(51) Int. Cl.
| | |
|---|---|
| *A61B 5/00* | (2006.01) |
| *A61M 16/04* | (2006.01) |
| *A61K 49/00* | (2006.01) |
| *A61B 5/08* | (2006.01) |

(52) U.S. Cl.
CPC .......... *A61B 5/4205* (2013.01); *A61B 5/0071* (2013.01); *A61K 49/0004* (2013.01); *A61M 16/0434* (2013.01); *A61M 16/0463* (2013.01); *A61B 5/0813* (2013.01)

(58) Field of Classification Search
CPC .. A61B 5/4205; A61M 16/04; A61M 16/0434
See application file for complete search history.

(56) References Cited

U.S. PATENT DOCUMENTS

| | | | | |
|---|---|---|---|---|
| 8,992,446 | B2 * | 3/2015 | Chau | A61B 5/4205 600/593 |
| 9,028,406 | B2 * | 5/2015 | Addington | A61B 5/04882 600/300 |
| 9,038,637 | B2 * | 5/2015 | Alqudah | A61M 16/0468 128/200.14 |
| 9,095,282 | B2 * | 8/2015 | Garde | A61B 5/103 |
| 9,138,171 | B2 * | 9/2015 | Chau | A61B 5/11 |
| 9,358,354 | B2 * | 6/2016 | Young | A61M 16/044 |
| 9,474,483 | B2 * | 10/2016 | Gribb | A61B 5/4205 |
| 9,526,856 | B2 * | 12/2016 | Azagury | A61M 16/0434 |
| 9,623,201 | B2 * | 4/2017 | Gregory | A61M 16/044 |

\* cited by examiner

*Primary Examiner* — Max Hindenburg
(74) *Attorney, Agent, or Firm* — Levisohn Berger LLP

(57) ABSTRACT

The invention provides a save and non-invasive alternative to the traditional modified Evans blue dye test for dysphagia in intubated patients. The method employs direct application of dye to the tongue, in combination with a tracheal tube that provides suction in the subglottal region above the cuff. By keeping the cuff inflated, the aspiration of food and liquid, as used in the traditional test, is avoided entirely.

2 Claims, 2 Drawing Sheets

NON-INVASIVE METHOD OF DIAGNOSING DYSPHAGIA IN PATIENTS HAVING A TRACHEOSTOMY

RELATED APPLICATIONS

Figure 1:
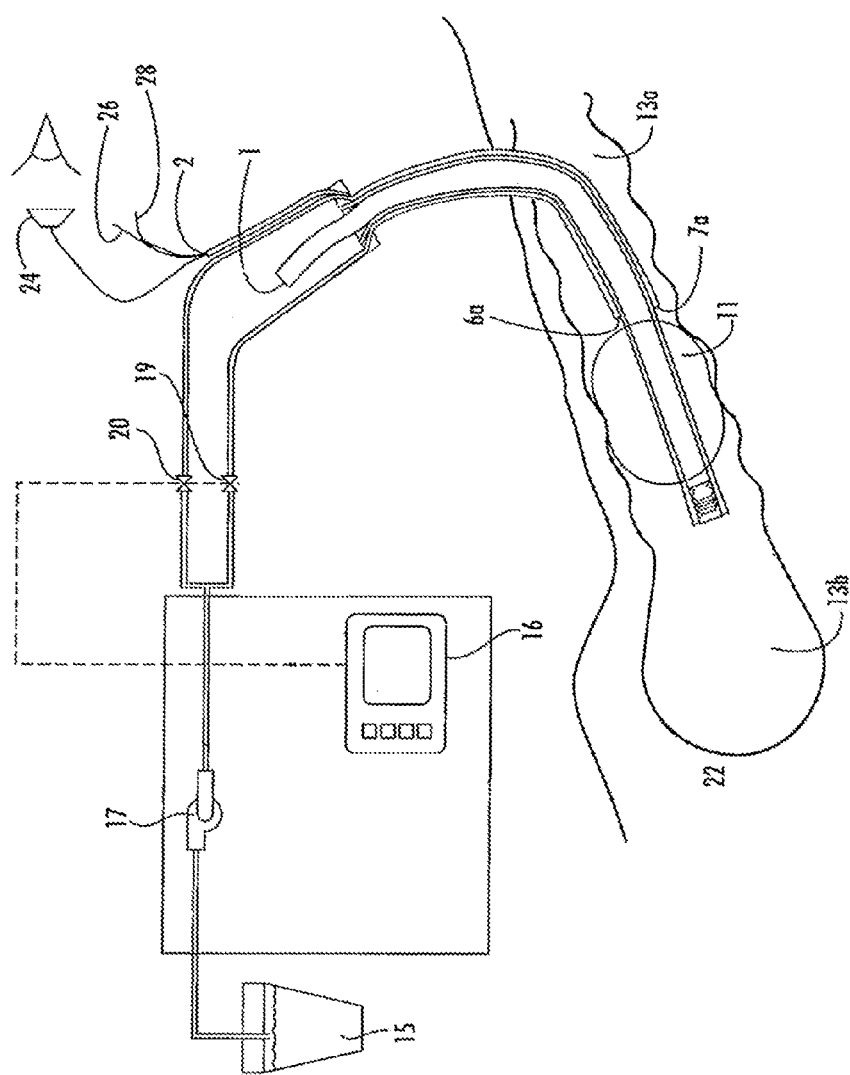

This application claims priority of U.S. provisional application No. 62/262,150 filed on Dec. 2, 2015, and U.S. provisional application No. 62/273,153 filed on Dec. 30, 2015, the entire contents of both of which are incorporated herein by reference.

FIELD OF THE INVENTION

The invention relates to an improved method and apparatus for diagnosing and evaluating dysphagia.

BACKGROUND OF THE INVENTION

Oropharyngeal dysphagia is a difficulty in swallowing, which arises from abnormalities of muscles, nerves or structures of the oral cavity, pharynx, and upper esophageal sphincter. Some patients have limited awareness of their dysphagia, and exhibit or complain of no symptoms, and in these cases the dysphagia may go undiagnosed and untreated. Such patients are at a high risk of pulmonary aspiration, and aspiration pneumonia secondary to food or liquids going the wrong way into the lungs. Patients presenting with "silent aspiration" do not cough or show outward signs of aspiration.

Tracheotomy is a surgical incision directly into the anterior aspect of the trachea for the purpose of establishing an artificial airway. A tube is placed into the surgically created opening to maintain the airway, resulting in what is usually referred to as a tracheostomy. Patients in hospital or long-term care settings are often intubated with a tracheal tube in order to assist in breathing, and patients with tracheostomies frequently have dysphagia or other swallowing problems. The resulting association between aspiration and tracheostomy has been well documented. (S. K. Epstein, *Respiratory Care* 2005, 50:542-549.) Due to the risk of aspiration pleumonia, is of critical importance for treating clinicians to identify and evaluate such problems.

At present, the fiberoptic endoscopic examination of the swallow (FEES) and the modified Evans blue dye test (MEBDT) are the standard examinations used by clinicians to detect swallowing disorders. MEBDT is much faster and simpler to perform, and detects about 85% of cases without the clinician having to resort to FEES. In administering the MEBDT, a clinician, such as a Speech and Language Pathologist, will dye a patient's food (e.g. applesauce) with a blue dye, deflate the cuff within the tracheal tube and then feed the dyed food to the patient. Subsequently, the clinician suctions the tracheal tube to collect fluids from the lower region of the tracheal tube. If the patient has dysphagia, then some of the dyed food will have entered the trachea and traveled to the region past the deflated cuff, so that when suctioning is performed, some of the dyed food will be present in the collected fluids. The presence of a swallowing disorder is confirmed upon identifying blue dye in the suctioned fluids.

The MEBDT has only moderate sensitivity and a poor negative predictive value, and it results in many missed diagnoses of swallowing disorders. (A. Fiorelli et al., *J. Cardiothoracic Vasc. Anesth.* 2016, 51053-0770:30295-6.) Moreover, the technique relies on several poorly controlled variables, including the duration of suctioning, the technique of the operator, and other factors which render MEBDT highly subjective. Moreover, the test relies on feeding foods to patients who potentially have a swallowing disorder, which may put patients at unnecessary risk, and is inapplicable where a patient is comatose or otherwise unable to cooperate.

There is therefore a need in the art for an improved method of evaluating swallowing disorders that is safer, more accurate and is less invasive to a patient, and requires little or no patient cooperation.

SUMMARY OF THE INVENTION

The invention set forth herein is a method of detecting or evaluating swallowing disorders using a minimally invasive method that is safe, highly accurate and well-tolerated by patients. In the inventive method, a patient is intubated with an endotracheal device which has a suctioning port above the cuff. Rather than feeding the patient dyed food, a clinician deposits several drops of dye on the back of a patient's tongue, and then suctions the subglottic region to determine whether or not any blue dye is present in the collected fluids. The presence of such dye indicates a swallowing disorder.

DETAILED DESCRIPTION OF THE INVENTION

Embodiments of the present invention will now be described with reference to the above-identified drawings. However, the drawings and the description herein of the invention are not intended to limit the scope of the invention. It will be understood that various modifications of the present description of the invention are possible without departing from the spirit of the invention. Also, features described herein may be omitted, additional features may be included, and/or features described herein may be combined in a manner different from the specific combinations recited herein, all without departing from the spirit of the invention.

The method of the invention makes use of a tracer which is any non-toxic substance that can be readily detected at low concentrations. Suitable materials may be dyes or leuco dyes, isotopic tracers, antigens, or enzymes, for which sensitive methods of detection are well known in the art. The most common, and most preferred tracer is Evans Blue, or T-1824, an azo dye that is readily detected by eye, and can be detected photometrically by absorbance at 626 nm, or by its fluorescence at 680 nm.

FIG. 1 is schematic view of a patient intubated with a tracheostomy tube. As shown, the tracheostomy tube has a central lumen 1, which is a channel allowing for the passage of air, usually provided by an external mechanical ventilator. The device is provided with an inflatable cuff or balloon 11 that, when inflated, separates the trachea into two regions. The first region, between the mouth and the balloon or the "superior region" 13a, also known as the subglottic region. The second region, between the lungs and the cuff, is the "inferior region" 13b. Distal to the inferior region 13b are the lungs 22. Optional elements that are typically present include a bore scope 24 inserted through a port 2 on the endotracheal tube to allow the practitioner to get a direct optical view of region 13b. Guide wires 26 and 28 are attached to the distal tip of the tracheal tube to provide directional guidance. A mechanical aspirator 17 applies suction for aspiration, which is regulated in the embodiment shown by valves 19 and 20, operated by a controller 16.

The particular tracheal device illustrated for use with the method of the invention has a pair of ports 6a and 7a allowing for the aspiration of mucus and other fluids. The invention is not limited to this design, and may be practiced with a wide variety of tracheostomy tubes available to the medical profession. It is only necessary that the device provides at least one suction port above the cuff 11, which is thereby located in the superior region 13a when the device is deployed in a patient. Manual aspiration (e.g., via a syringe) may be used, but in a preferred embodiment of the invention, an aspirator 17 is used to create negative pressure in order to draw fluids and deliver them to an external canister 15. The aspirator may be any vacuum suctioning device, such as an impeller pump, a rotary vane pump or similar suctioning devices known in the art.

Figure 2:
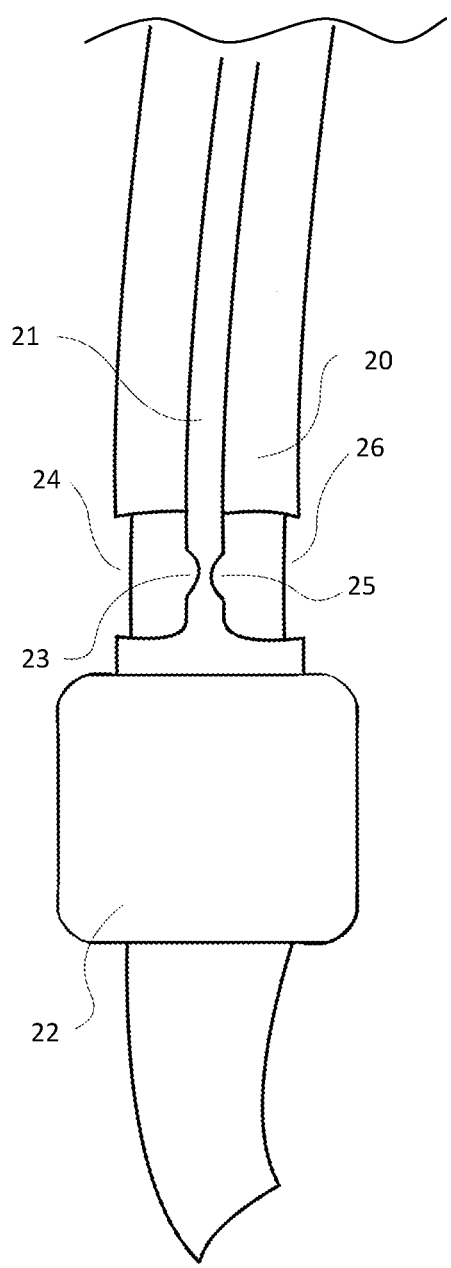

FIG. 2 illustrates the cuff and distal end of an alternative tracheal tube, also useful in the practice of the invention, seen in a side-on view. Fused to, or intergral with, the visible side of the airway tube 20 is a lumen 21 connected to an external vaccum source, preferably an aspirator pump. The lumen has a port 23 opening onto a recessed channel 24 on the dorsal side of the tube, and a second port 25 opening onto a seconed recessed channel 26 on the ventral side of the tube. The two channels are not contiguous, being separated on the far side by a similar lumen (not shown). The function of the other lumen is not relevant to the present invention; it may provide air for inflating cuff 22, vacuum for aspirating the tracheal area distal to the cuff, or fluids for lavage of the trachea. This design is useful in that the channels 24 and 26 each subtend essentially 180° of arc around the tube, and together provide essentially 360° of coverage. The presence of a second port and channel on the dorsal side, located close to the cuff, enables this design to collect fluids collecting above the cuff on the dorsal side of the tube, as will occur in a patient who is in a reclining or semi-reclining position.

In the prior art method of administering the MEBDT, a clinician first deflates the cuff and subsequently feeds dye-treated food to a patient. Some time thereafter, the inferior region of the trachea (13b in FIG. 1) is suctioned, by any of various means known in the art. Any food (and dye) that may have entered the trachea and traveled past the deflated cuff into the inferior region is collected via such suctioning, and the collected aspirate is examined for the presence of the dye. Any such aspiration of food into the inferior region, however, carries with it the risk of infection.

In the method of the invention, on the other hand, the cuff is left inflated so that no aspirated material can travel past it into the inferior region. The practitioner deposits several drops of a solution of a tracer on a patient's tongue, and the patient, if cooperating, swallows. After several minutes to allow any tracer entering the trachea to reach the cuff, the practitioner subsequently suctions the superior region (13a in FIG. 1) via the suction ports (6a and 7a in FIG. 1; 23 and 25 in FIG. 2). Any fluid suctioned from the superior region is collected (e.g. in external canister 15) and evaluated for the presence of the tracer. The presence of tracer in the fluid in canister 15 is indicative of a swallowing disorder. That is, if a patient has a swallowing disorder, then the tracer deposited on his/her tongue would travel into the trachea and collect in the superior region 13a above the cuff. Thus, upon detection of tracer from the fluids of the superior region, the presence of a swallowing disorder is identified.

The inventive method is a significant improvement over the prior art procedure. For example, the method does not require that a patient ingest foods and it does not require that the tracer travel all the way to the inferior region to be collected. Rather, to the extent that fluid enters the trachea, it will gather in the superior (subglottic) region and it will not move farther down the trachea. Thus, the inventive method is an objective test that is safe, highly accurate and well tolerated by patients.

Having described this invention with regard to specific embodiments, it is to be understood that the description is not meant as a limitation since further modifications and variations may be apparent or may suggest themselves to those skilled in the art. It is intended that the present application cover all such modifications and variations.

I claim:

1. A method for diagnosis of a swallowing disorder in a subject intubated with a tracheostomy tube having a cuff, comprising the steps of
    inflating the cuff of the trachesostomy tube,
    depositing a solution of a tracer on the subject's tongue,
    suctioning fluid from the subglottic region above the cuff, and
    determining whether the tracer is present in the fluid;
wherein the presence of the tracer in the fluid indicates that the subject is suffering from a swallowing disorder.

2. The method of claim 1, wherein the tracer is Evans Blue dye (T-1824, C.I. Direct Blue 53).

* * * * *